(12) United States Patent
Sherwinter (10) Patent No.: US 8,840,638 B2
(45) Date of Patent: Sep. 23, 2014

(54) LAPAROSCOPIC RETRACTOR

(76) Inventor: Danny A. Sherwinter, Brooklyn, NY (US)

(*) Notice: Subject to any disclaimer, the term of this patent is extended or adjusted under 35 U.S.C. 154(b) by 83 days.

(21) Appl. No.: 13/370,168

(22) Filed: Feb. 9, 2012

(65) Prior Publication Data

US 2012/0209075 A1    Aug. 16, 2012

Related U.S. Application Data

(60) Provisional application No. 61/457,249, filed on Feb. 10, 2011.

(51) Int. Cl.
*A61B 17/00* (2006.01)
*A61B 17/02* (2006.01)
*A61B 17/29* (2006.01)

(52) U.S. Cl.
CPC ..... *A61B 17/0218* (2013.01); *A61B 2017/2927* (2013.01); *A61B 2017/2906* (2013.01); *A61B 17/29* (2013.01)
USPC .......................................... 606/205; 606/208

(58) Field of Classification Search
USPC ............ 600/204, 209, 210, 215, 218; 606/48, 606/51, 52, 205–211
See application file for complete search history.

(56) References Cited

U.S. PATENT DOCUMENTS

| | | |
|---|---|---|
| 4,655,219 A | 4/1987 | Petruzzi |
| 5,201,752 A | 4/1993 | Brown |
| 5,215,101 A | 6/1993 | Jacobs |
| 5,350,391 A | 9/1994 | Iacovelli |
| 5,441,494 A | 8/1995 | Ortiz |
| 5,474,057 A * | 12/1995 | Makower et al. ............. 600/214 |
| 5,496,310 A | 3/1996 | Exconde |
| 5,766,205 A | 6/1998 | Zvenyatsky |
| 2003/0208185 A1 | 11/2003 | Sheffer |
| 2006/0142644 A1 | 6/2006 | Mulac |
| 2008/0045803 A1* | 2/2008 | Williams et al. ............. 600/204 |
| 2008/0262513 A1 | 10/2008 | Stahler |
| 2009/0171373 A1 | 7/2009 | Farritor |
| 2010/0262162 A1 | 10/2010 | Omori |
| 2011/0112434 A1 | 5/2011 | Ghabrial |

OTHER PUBLICATIONS

Apollo Industries 2011 Product Catalog.
Aesculap, Inc. 2010 Product Catalog.
International Search report dated Jun. 7, 2012 from PCT/US2012/024738.
Written Opinion dated Jun. 8, 2012 from PCT/US2012/024738.

* cited by examiner

*Primary Examiner* — David Bates
*Assistant Examiner* — Samuel Hanna (57) ABSTRACT

The present invention provides a retractor for use during laparoscopic cholecystectomy.

6 Claims, 10 Drawing Sheets

LAPAROSCOPIC RETRACTOR

CROSS-REFERENCE TO RELATED APPLICATIONS

The present application claims the benefit of U.S. Provisional Application Ser. No. 61/457,249, filed Feb. 10, 2011, the entire contents of which are incorporated by reference.

FIELD OF THE INVENTION

The present invention generally relates to a retractor for use during laparoscopic cholecystectomy (LC).

BACKGROUND OF THE INVENTION

Cholecystectomy is the surgical removal of the gallbladder. Surgical options include open cholecystectomy and LC. A traditional open cholecystectomy involves removal of the gallbladder through a large open incision to the abdomen, thus sometimes requiring a lengthy recovery time for a patient. A traditional open cholecystectomy will also leave a subcostal scar on the patient due to the large incision required.

LC has mainly supplanted open cholecystectomies as the preferred surgical method for removing gallbladders. A LC typically involves making several small incisions in the abdomen to create various operating ports for the insertion of instruments such as small cylindrical tubes (for the insertion of the retractor) and a video camera for monitoring the surgery. The video camera illuminates the surgical field and sends a magnified image from inside the abdomen to a video monitor, giving the surgeon a close-up view of the gallbladder and surrounding tissues. This allows the surgeon to finely control the surgical instruments inserted into the patient.

Figure 1:
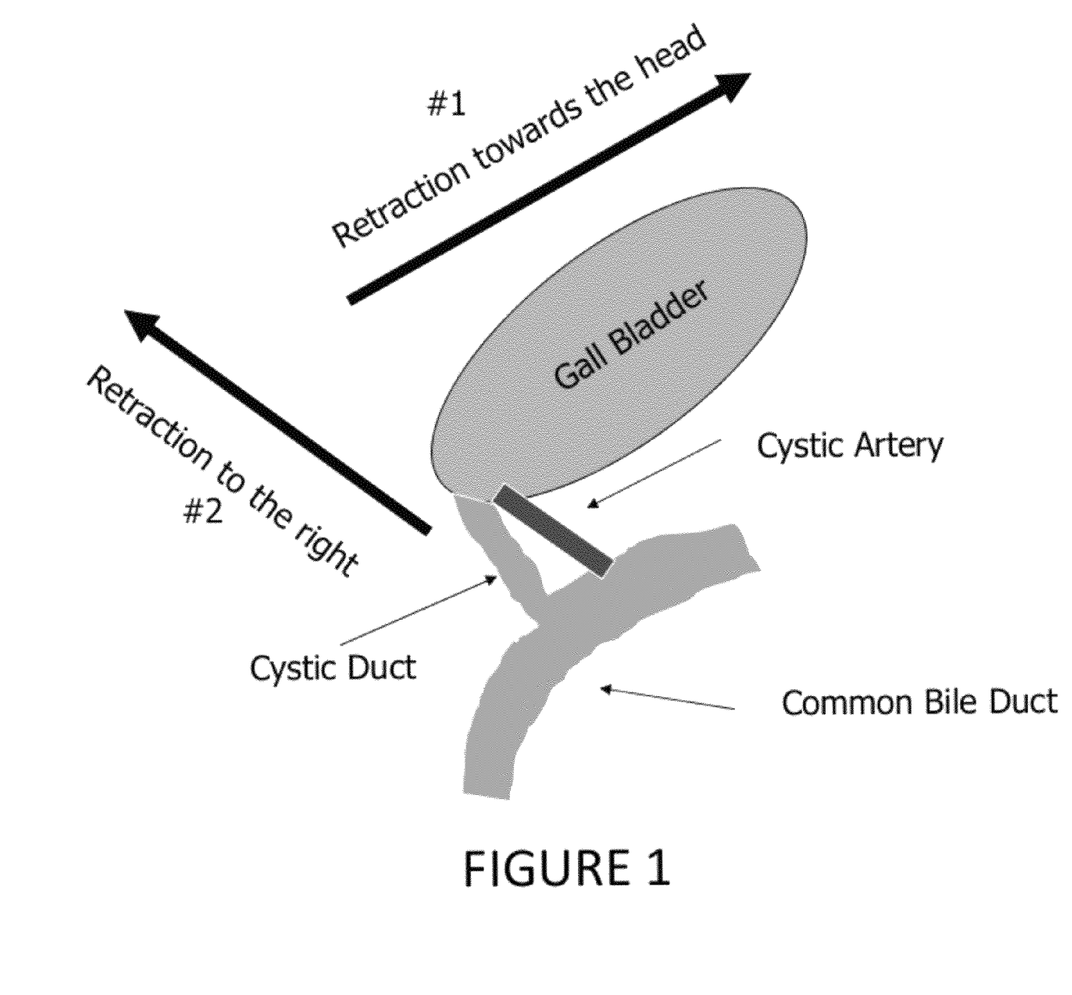
FIG. 1 is a diagram depicting how the gallbladder is retracted to reveal the cystic duct and cystic artery prior to removal of the gallbladder.

To perform LC, a patient is placed on the operating table and anesthetized. Then, using a Veress needle or Hasson technique, the abdominal cavity is entered. The surgeon inflates the abdominal cavity with carbon dioxide or other inert gas to create a working space. The video camera is placed through the umbilical port and the abdominal cavity is inspected. A first retractor is inserted through a first port and the fundus is retracted cephalad. A second retractor, inserted through a second port, is used to retract the infundibulum laterally (as shown in FIG. 1). This allows the cystic duct and cystic artery to be identified through the video camera and be dissected using a dissector. Next, the gallbladder is dissected away from the liver bed and removed through one of the ports. For a detailed example of LC using two graspers see U.S. Pat. No. 5,496,310, the contents of which are incorporated by reference in their entirety.

Recently, LC has been performed through a single incision via the patient's umbilicus as the only incision. This advanced technique is called Laparoendoscopic Single Site Surgery (LESS). However, LESS requires that the video camera, dissector, and two retractors all be inserted through the single incision in the patient's umbilicus. The need for four instruments all vying for space and mobility through the one incision at the umbilicus is too unwieldy. Therefore, a need clearly exists for a single instrument capable of performing the function(s) of the two separate retractors.

SUMMARY OF THE INVENTION

Generally, the present invention provides a laparoscopic retractor that has a single shaft having a proximal and a distal end. The distal end of the shaft ends in a T-like appendage attached by 1 or more hinges to the shaft. The hinges allow the T-like appendage to swivel and/or rotate independently of the shaft. The proximal end of the shaft ends in a handle so that the surgeon can manipulate the retractor after it is inserted into the abdominal cavity of a patient. The proximal and distal ends of the T-like appendage each have a grasper that can be actuated by the surgeon.

Other objects, features, and characteristics of the present invention, as well as the methods of operation and functions of the related elements of the structure, and the combination of parts and economies of manufacture, will become more apparent upon consideration of the following detailed description with reference to the accompanying drawings, all of which form a part of this specification.

BRIEF DESCRIPTION OF THE DRAWINGS

For a more complete understanding of the present invention, reference is now made to the following drawings in which.

DETAILED DESCRIPTION OF THE PREFERRED EMBODIMENTS

As required, a detailed illustrative embodiment of the present invention is disclosed herein. However, techniques, systems and operating structures in accordance with the present invention may be embodied in a wide variety of forms and modes, some of which may be quite different from those in the disclosed embodiment. Consequently, the specific structural and functional details disclosed herein are merely representative.

Figure 2:
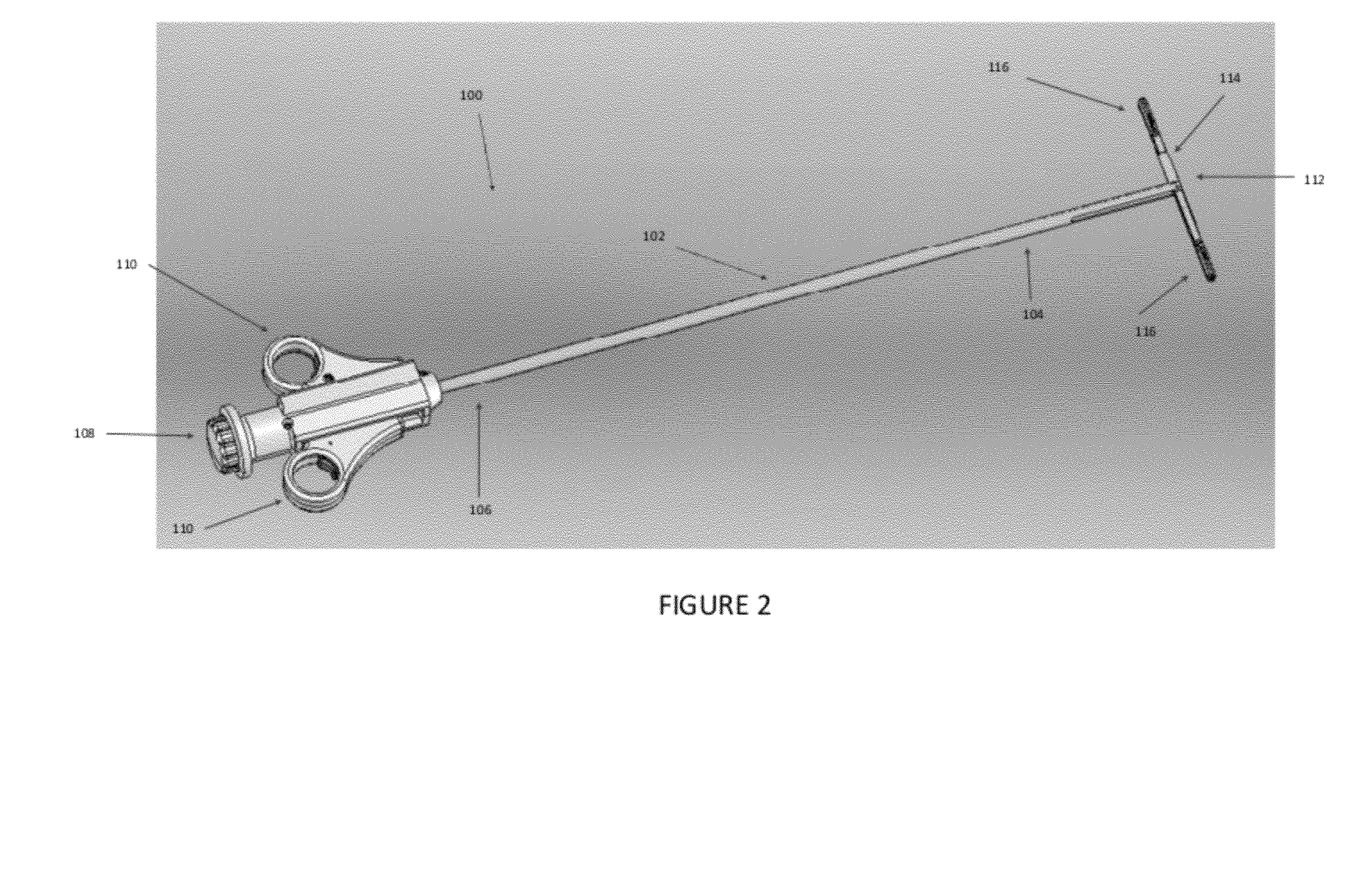
FIGS. 2-2D is an open view of the laparoscopic retractor in accordance with one embodiment of the present invention.

Referring first to FIG. 2, depicted is an open view of the laparoscopic retractor 100 in accordance with one embodiment of the present invention. As shown, laparoscopic retractor 100 comprises shaft 102, handle 108, actuating mechanisms 110, pivot joint 112, and appendage 114. Appendage 114 further comprises graspers 116 located at each end that can be opened/closed by advancing actuating mechanisms 110 from the distal end (106) of shaft 102 toward the proximal end (104) (as shown in FIGS. 2B-2D). In a preferred embodiment, the laparoscopic retractor 100 is constructed from stainless steel and medical grade plastics (i.e., materials that are easily sterilized). The graspers can be oriented as shown or curved so as to more easily grasp the gall bladder as needed. Preferably, shaft 102 is approximately 35-50 cm in length while appendage 114 is 3-5 cm in length.

Figure 2A:
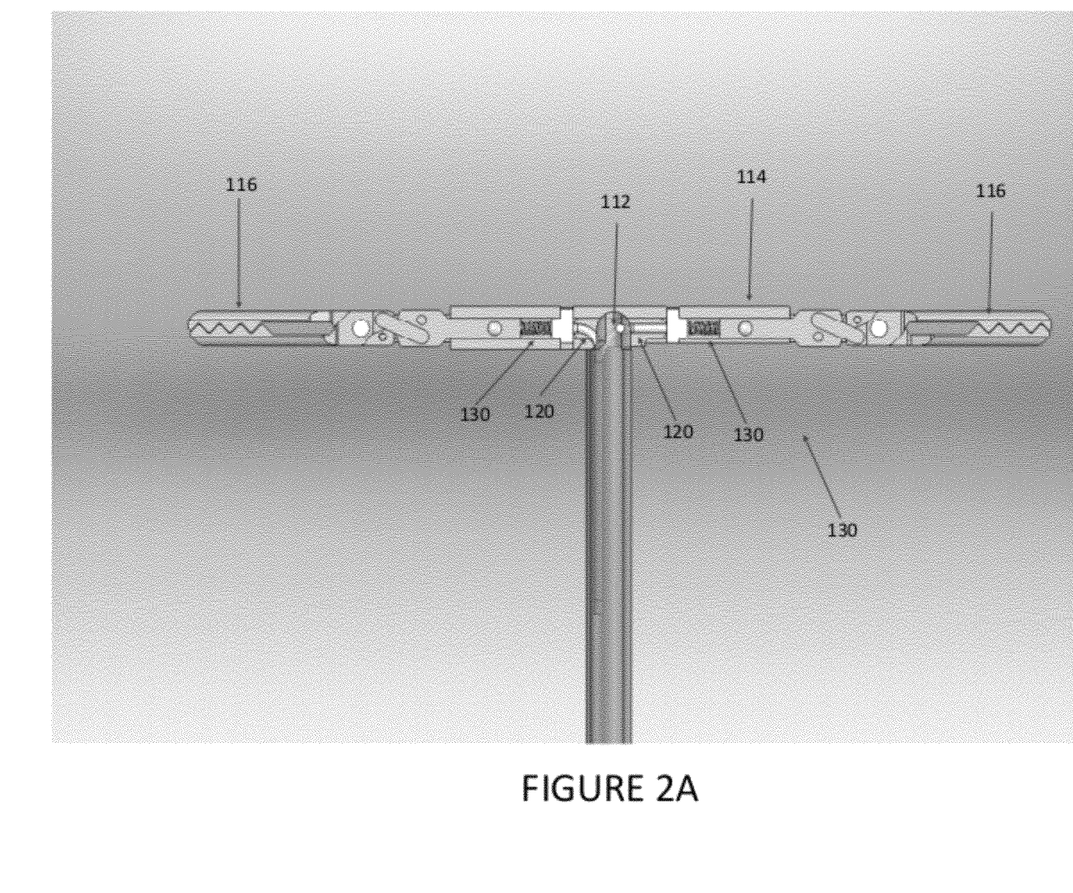
Figure 2B:
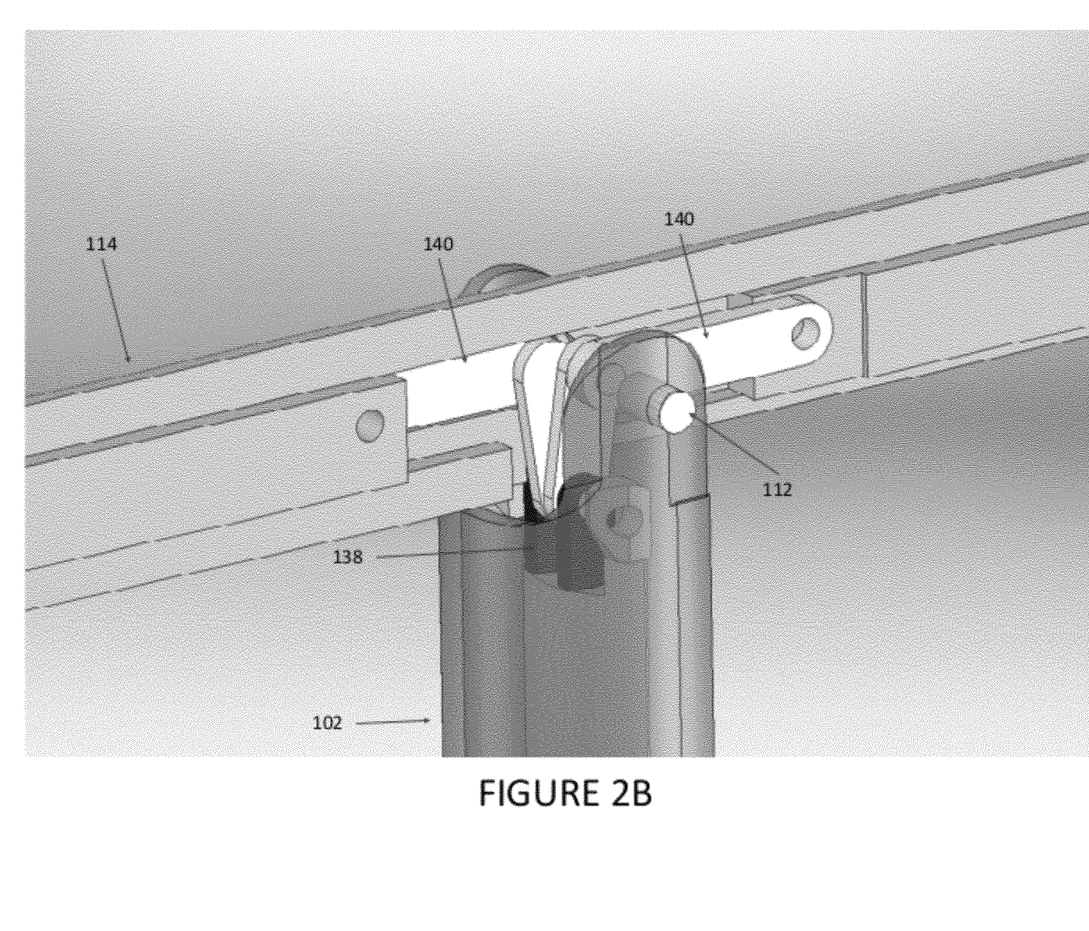
Figure 2C:
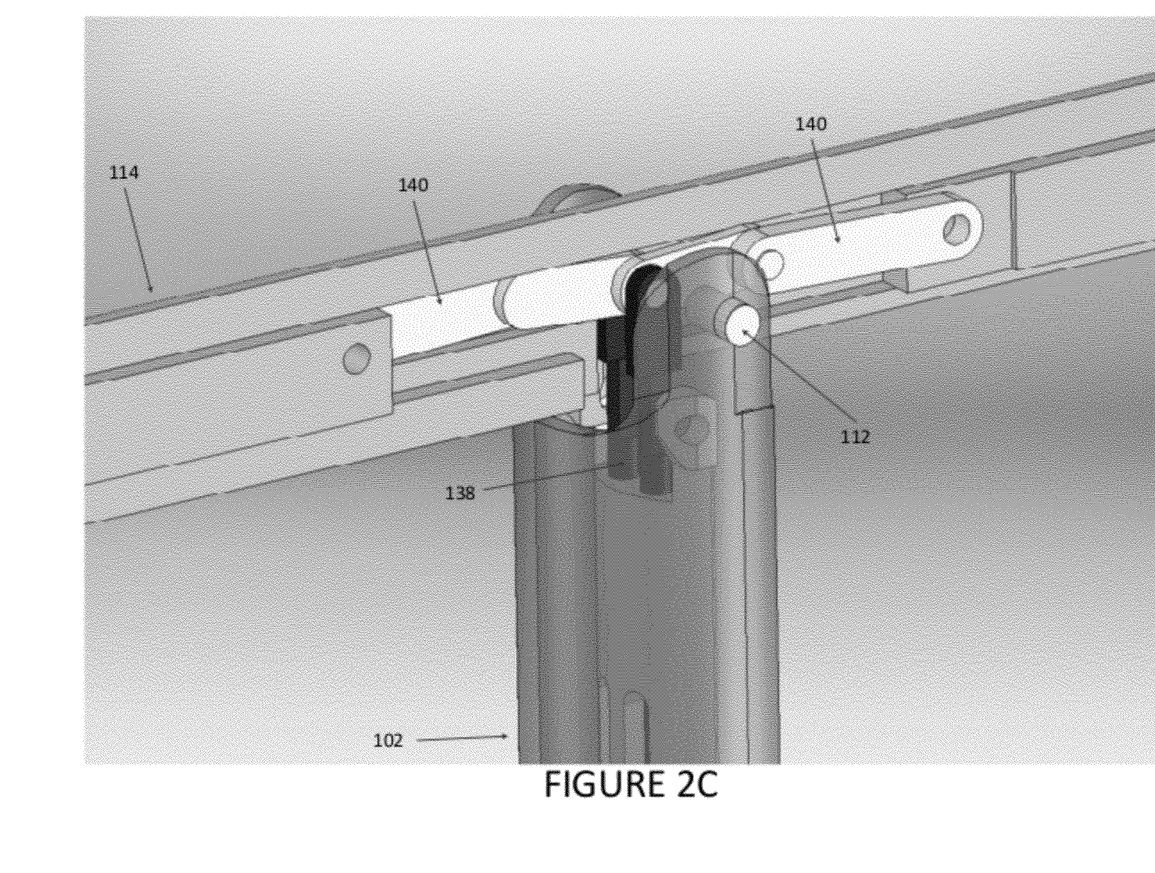
Figure 2D:
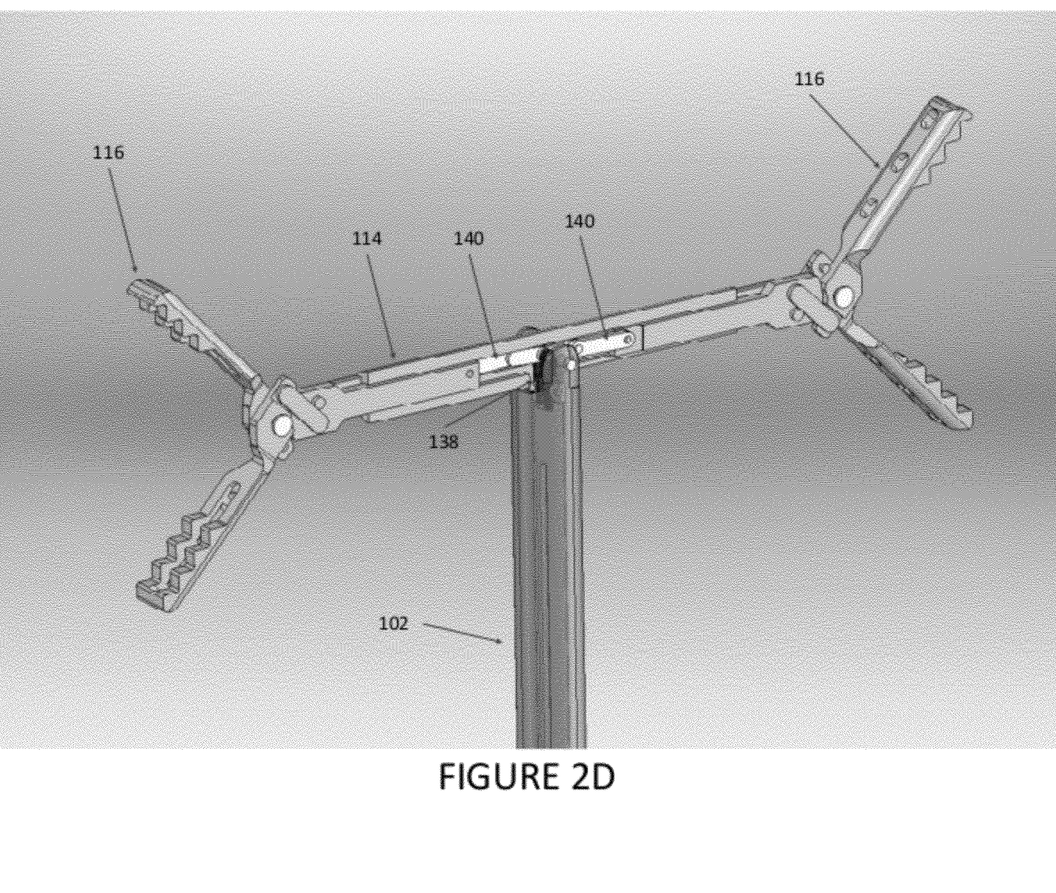

In one embodiment of the design, as shown in FIG. 2A, each actuating mechanism 110 can control its respective grasper 116 by engaging a wire encased in a sheath 120 that runs down shaft 102. Springs 130, located in appendage 114, provide the tension that allows graspers 116 to move between an open position and a closed position.

In another embodiment, as shown in FIGS. 2B-2D, the graspers 116 can be opened by the interaction of press 138 and hinged actuating mechanisms 140. FIG. 2B depicts appendage 114 in an open position with graspers 116 in a closed position. Press 138 is located at a first position within shaft 102 and hinged actuating mechanisms are is in an initial bent position. As a user actuates actuating mechanisms 110 press 138 advances toward the distal end of shaft 102, which in turn causes hinged actuating mechanisms 140 to advance into appendage 114 such that hinged actuating mechanisms 140 are substantially linear as shown in FIG. 2C. The advancement of hinged actuating mechanisms 140 into appendage 114 causes graspers 116 to open as shown in FIG. 2D.

Figure 2E:
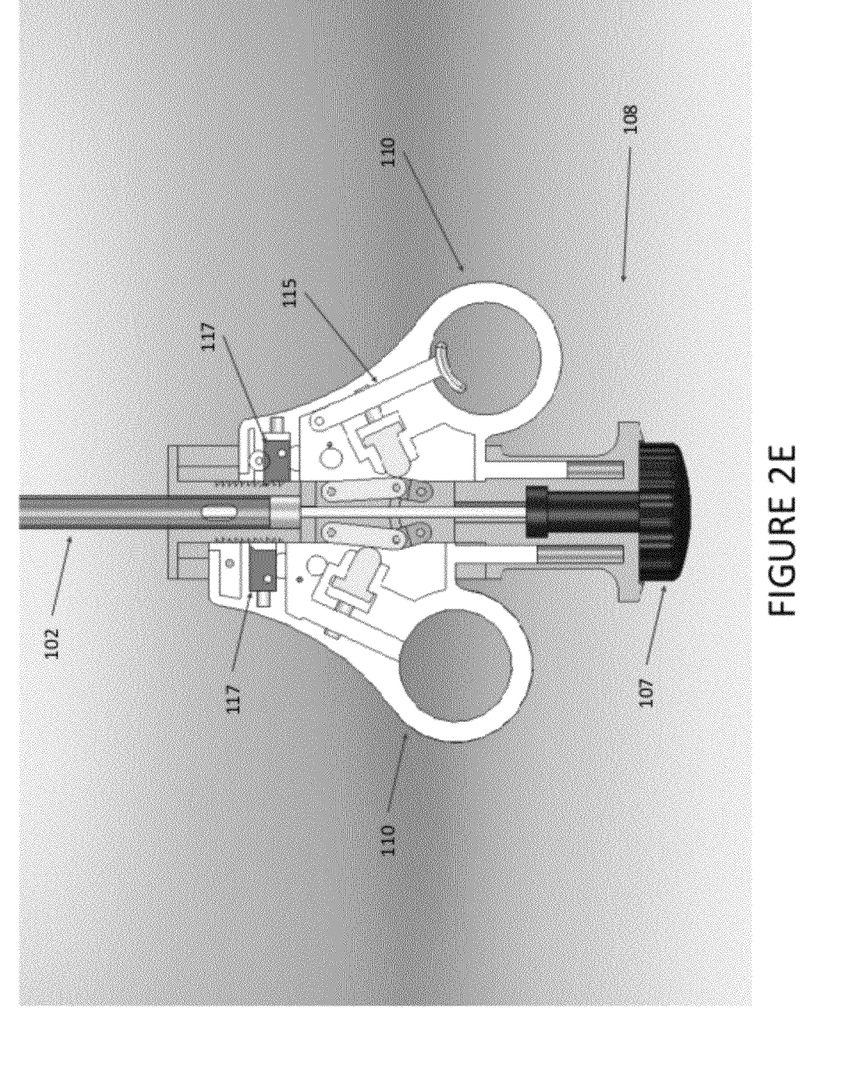
FIGS. 2E-2F are enhanced views of the handle of the laparoscopic retractor.
Figure 2F:
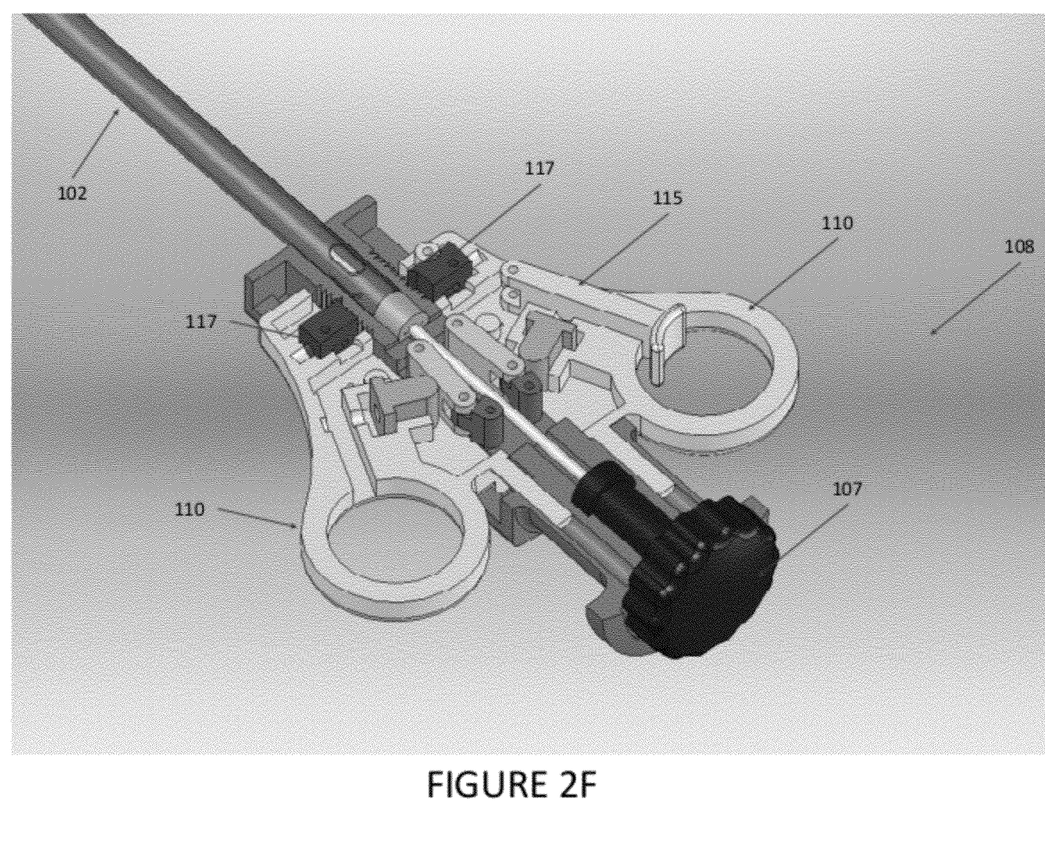
Figure 3:
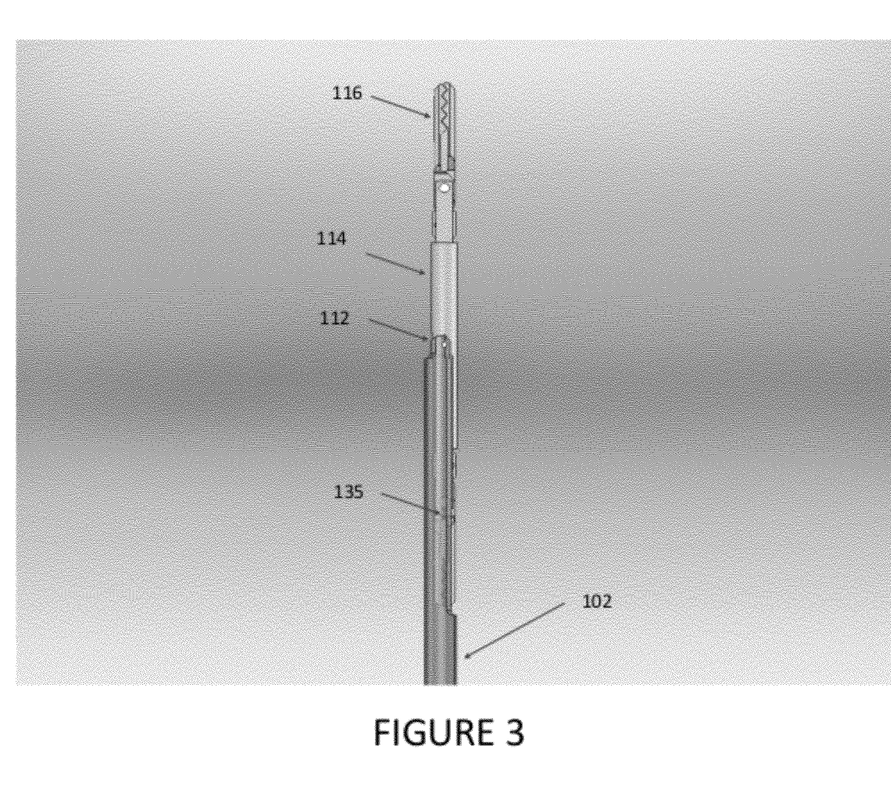
FIGS. 3 and 3A show a closed view of the laparoscopic retractor
Figure 3A:
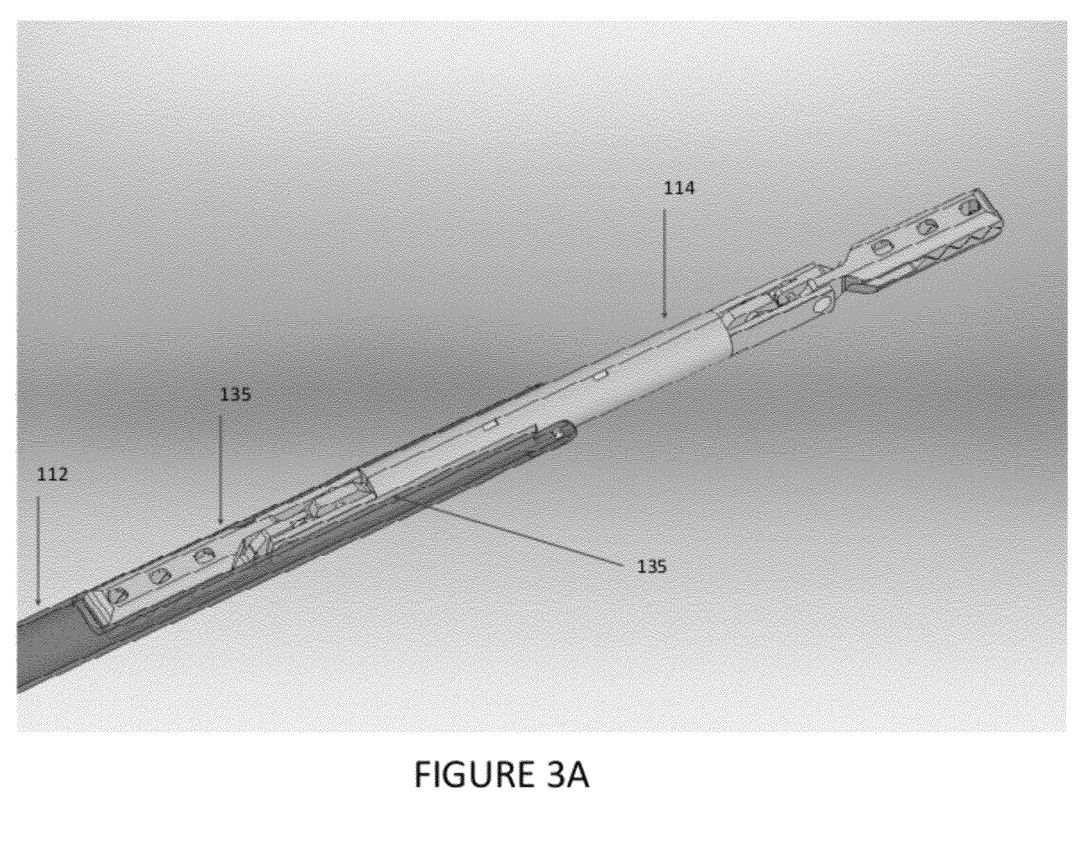

FIGS. 2E and 2F depicted enhanced views of handle 108 of laparoscopic retractor 100. As shown, handle 108 comprises tab 115 and ratchet mechanism 117 which can be used to lock the actuating mechanisms 110 in a closed configuration, thereby locking the graspers 116 in a closed configuration as needed. Knob 107, located in handle 108 that when turned drives a rod up the shaft 102 and acts to rotate the appendage 114 about the pivot joint 112 from horizontal to vertical (as shown in FIGS. 3 and 3A). Additional methods for actuating the graspers, such as placing tabs on the appendage 114 which when squeezed actuate the graspers or other methods of attaching the gall bladder to the appendage such as with suction, clips, or hooks, are also be envisioned.

To use laparoscopic retractor 100 during a LESS operation, the appendage 114 would first be pivoted about pivot joint 112 so that it appears as in FIGS. 3 and 3A. By holding handle 108, a surgeon can then guide laparoscopic retractor 100 into the abdominal cavity, similar to a standard retractor. The appendage 114 can be rotated into the working/horizontal position by either pushing the appendage up to the abdominal wall thus flipping the appendage into the horizontal position or by rotating the knob in the handle and driving a rod up the shaft to rotate the appendage into the horizontal position as shown in FIG. 1. When the appendage 114 is in a closed position, it resides in groove 135 located in shaft 102.

Appendage 114 is then rotated into its opened position as shown in FIG. 2A. By using each actuating mechanism 108, the graspers 116 can be separately actuated as shown in FIG. 2D to allow attachment of laparoscopic retractor to the gallbladder fundus and infundibulum.

By rotating shaft 102 of laparoscopic retractor 100, retraction of the gallbladder can be achieved, thus allowing the surgeon to sever the cystic duct and the cystic artery. The gallbladder can then be removed from the abdominal cavity using any known method. For example, a dissector tool can then be inserted to perform the removal of the gallbladder.

In another embodiment, the handle of the laparoscopic instrument 100 can have a connection at the handle 108 that can either clip to the drapes or the bed in the operating room to stabilize the instrument in one position, thus avoiding the need for an assistant. The attachment can be made in the form of a clip, clamp, magnetic attachment or any other similar attaching method. The shaft 102 of the instrument can also be bent in such a way as to keep the shaft out of the operative field. In another embodiment of the device instead of a linear bar, two curved grasping elements can be placed at the termination of the shaft 102 in such a way so that, in their native position, both graspers are curved in the same direction but can be rotated around the center position bringing them to oppose each other and face in opposite directions thereby approximating a similar T shaped formation.

While the present invention has been described with reference to one or more preferred embodiments, which embodiments have been set forth in considerable detail for the purposes of making a complete disclosure of the invention, such embodiments are merely exemplary and are not intended to be limiting or represent an exhaustive enumeration of all aspects of the invention. The scope of the invention, therefore, shall be defined solely by the following claims. Further, it will be apparent to those of skill in the art that numerous changes may be made in such details without departing from the spirit and the principles of the invention.

What is claimed is:

1. A laparoscopic retractor comprising:
a shaft having a proximal end and a distal end, wherein the distal end of the shaft comprises a lengthwise groove open axially along a first sidewall of the shaft;
a handle connected to the proximal end of the shaft, wherein the handle comprises at least one actuating mechanism connected to the handle; and
an appendage having a proximal end and a distal end rotatably connected to the distal end of the shaft, wherein the appendage is attached to the distal end of the shaft using a pivot joint, said appendage comprising:
a first grasper mounted on the proximal end of the appendage; and
a second grasper mounted on the distal end of the appendage,
wherein the at least one actuating mechanism configured to open and close the first grasper or the second grasper using a wire located in a sheath connected to the first grasper or second grasper and to the at least one actuating mechanism,
wherein one of the ends of the appendage rotates into the lengthwise groove when the appendage is in a closed, such that a lengthwise axis of the shaft and a lengthwise of the appendage are parallel when the apendage is in the closed position, and
wherein the lengthwise axis of the shaft and the lengthwise axis of the appendage are at an angle relative to one another and not being parallel when the appendage is in an open position.

2. The laparoscopic retractor of claim 1, wherein the first grasper and the second grasper are curved.

3. The laparoscopic retractor of claim 1, wherein the laparoscopic retractor is constructed from stainless steel and medical grade plastics.

4. The laparoscopic retractor of claim 1, wherein the at least one actuating mechanism is adapted to open and close the first grasper; and
a second actuating mechanism is adapted to open and close the second grasper.

5. The laparoscopic retractor of claim 4, wherein the first actuating mechanism is connected to the first grasper via the wire located in a sheath; and
the second actuating mechanism is connected to the second grasper via a second wire located in a second sheath.

6. The laparoscopic retractor of claim 1, wherein the first grasper and the second grasper contain interlocking teeth.

* * * * *